United States Patent [19]
Bucala et al.

[11] Patent Number: 5,811,401
[45] Date of Patent: Sep. 22, 1998

[54] ADVANCED GLYCOSYLATION ENDPRODUCTS AND METHODS OF USE THEREFOR

[75] Inventors: Richard J. Bucala; Yousef Al-Abed, both of New York, N.Y.

[73] Assignee: The Picower Institute for Medical Research, Manhasset, N.Y.

[21] Appl. No.: 757,234

[22] Filed: Nov. 27, 1996

Related U.S. Application Data

[60] Provisional application No. 60/007,785 Nov. 30, 1995.
[51] Int. Cl.⁶ .................................................. A61K 38/05
[52] U.S. Cl. ........................... 514/19; 530/331; 530/345; 514/17; 514/18; 562/560; 562/562
[58] Field of Search .................................. 530/331, 345; 514/19; 536/22; 562/560, 562

[56] References Cited

U.S. PATENT DOCUMENTS

| | | | |
|---|---|---|---|
| 5,214,138 | 5/1993 | Monnie | 536/17.3 |
| 5,238,963 | 8/1993 | Cerami | 514/632 |
| 5,334,617 | 8/1994 | Ulrich | 514/562 |
| 5,480,807 | 1/1996 | Monnie | 436/86 |
| 5,624,804 | 4/1997 | Bucala | 435/7.1 |

FOREIGN PATENT DOCUMENTS

| | | |
|---|---|---|
| WO 93/13421 | 7/1993 | WIPO . |
| WO 94/20083 | 9/1994 | WIPO . |

OTHER PUBLICATIONS

Araki et al. (1992) J. Biol. Chem. 267:10211–4.
Brownlee et al. (1983) J. Exp. Med. 158:1739–44.
Bucala et al. (1993) Proc. Natl. Acad. Sci. USA 90:6434–8.
Cohen et al. (1994) Kidney International 45:1673–9.
Harris et al. (1993) TIBTECH 11:42–46.
Horiuchi et al. (1991) J. Biol. Chem. 266:7329–32.
Kohn et al. (1984) Diabetes 33:57–9.
Makita et al. (1992) J. Biol. Chem. 267: 5133–8.
Makita et al. (1992) Science 258:651–3.
Nakayama et al. (1989) Biochem. Biophys. Res. Commun. 162:740–5.
Al–Abed, Bioorganic Med Chem Lett. 5, 2929, 1995.

*Primary Examiner*—Cecilia J. Tsang
*Assistant Examiner*—David Lukton
*Attorney, Agent, or Firm*—Klauber & Jackson

[57] ABSTRACT

The present invention relates to advaced glycosylation endproducts formed by the reaction of arginine-lysine or lysine-arginine dipeptides, optionally as part of a larger protein or amino-containing-biomolecule, with reducing sugars. These AGEs can be used in various diagnostic and therapeutic methods.

6 Claims, 1 Drawing Sheet

1

ADVANCED GLYCOSYLATION ENDPRODUCTS AND METHODS OF USE THEREFOR

This Application claims priority from U.S. Provisional application Ser. No. 90/007,785, filed Nov. 30, 1995.

This invention was made with partial assistance from a grant, DK19655 "Biochemical Basis of the Complications of Diabetes," from the National Institute of Diabetes and Digestive and Kidney Diseases of the National Institutes of Health.

The Applicants of the instant invention are co-authors of the following publications, published after the above-mentioned priority filing: Al-Abed et al., *Bioorganic and Medicinal Chemistry Letters*, 5:23, pp. 2929–2930 (1995), and Al-Abed et al.in *Peptides: Chemistry, Structure and Biology*, ed. by Pravin et al., Mayflower Scientific Ltd. (1996).

BACKGROUND OF THE INVENTION

The present invention relates generally to the aging of proteins and other amino-containing-biomolecules resulting from reaction of glucose, and particularly to the non-enzymatic glycation or glycosylation of proteins and other susceptible amine-presenting molecules and subsequent reactions leading to advanced glycosylation end products, and to methods for their use.

The reaction between glucose and proteins has been known for many years. Its earliest manifestation was in the appearance of brown pigments during the cooking of food, which was identified by Maillard in 1912, who observed that glucose or other reducing sugars react with amino-containing compounds, including amino acids and peptides, to form adducts that undergo a series of dehydrations and rearrangements to form stable brown pigments.

In the years that followed the initial discovery by Maillard, food chemists studied this reaction in detail and determined that stored and heat-treated foods undergo non-enzymatic browning as a result of the reaction between glucose and the polypeptide chain, and that the proteins are resultingly crosslinked and correspondingly exhibit decreased bioavailability. At this point, it was determined that the pigments responsible for the development of the brown color that develops as a result of protein glycosylation possessed characteristic spectra and fluorescent properties.

As a result of the recent interest in this area, the first few stages of the Maillard reaction, and a relatively limited number of associated initial adducts and products, have become well-known. As subsequent reactions (including various dehydrations, oxidations, eliminations, condensations, cleavages, and other chemical changes) occur, however, a bewildering array of "early" and "late" glycation adducts and reactants is generated, and these are less well understood in molecular detail. As a group, the more advanced glycation adducts can be described as a class of yellow-brown, fluorescent pigments with intra- and inter-molecular crosslinking activity, wherein specific glycation entities are thought to occur at low abundance within the widely divergent pool of advanced glycation end products (or AGEs). Despite significant work over the last twenty years or so, the molecular structures of only a few of these later glycation adducts and products have been determined, and the contribution of identified, in vivo-formed advanced glycation structures to specific biological processes remains poorly understood.

Advanced glycosylation endproducts (AGEs) have been linked to the development of many of the long-term complications of diabetes, renal insufficiency, and normal aging. Although the structures of the most abundant AGEs which occur in vivo are unknown, Monnier et al. recently isolated the fluorescent crosslink pentosidine from human dura collagen. Pentosidine appears to form as the condensation product of lysine, arginine, and a reducing sugar precursor. In vitro, pentosidine may be readily produced upon incubation of the N-alpha-protected derivatives of arginine, lysine, and sugars such as ribose, glucose, fructose, ascorbate, or dehydroascorbate.

Measurements of pentosidine content in a variety of biological specimens have revealed that this bi-functional condensation product accounts for only a small percentage (<1%) of potential glucose-derived crosslinks. Furthermore, when bovine serum albumin (BSA), which contains 59 lysine and 23 arginine residues, is incubated with D-glucose in phosphate buffer, pentosidine forms in a yield of only 1 mmol/mol protein. It also has been noted that while many proteins such as ovalbumin and BSA can undergo a high degree of modification or "impairment"of lysine and arginine residues during advanced glycosylation, protein oligomerization rarely ensues.

A large body of evidence has been assembled to show that Maillard products as a whole underlie a wide variety of both normal and pathogenic activities and responses that occur as advanced glycation end products (or AGEs) accumulate in vivo. Such activity may be direct, as a consequence of the chemical reactivity of glycation products and adducts, or indirect, mediated by the cellular recognition of glycation adducts and products via AGE-specific binding proteins or receptors. An appreciation for the pathogenic potential of AGEs has suggested that interference with, or inhibition of, advanced glycation chemistry could be of enormous therapeutic benefit. The agent pimagidine (aminoguanidine), and other related compounds, have been found to be useful glycation inhibitors. This compound, and others like it, has been theorized to react with the carbonyl moiety of the early glycosylation product of a target protein formed subsequent to the initial non- enzymatic reaction with glucose or another reducing sugar, and thereby prevent further reaction to form advanced glycosylation end products.

Recently, it has been discovered that other naturally-occurring reducing sugars, including fructose, ribose and galactose, participate in non-enzymatic glycation and cross-linking. Thus, the formation of equivalent AGEs with fructose and other reactive sugars present in vivo or in foodstuffs, including ribose and galactose, are anticipated in the present invention.

SUMMARY OF THE INVENTION

In accordance with the present invention, model advanced glycosylation endproducts (AGEs) have been prepared which examine the contributions of intramolecular crosslinking of adjacent amino acid residues to the formation of novel pentosidine-type (ansa-macrocycle) AGEs in model systems. The thus prepared AGEs find utility as both therapeutic and diagnostic agents, and the present invention also concerns their methods of use in these areas.

The present invention also has particular diagnostic applications as the Maillard process acutely affects several of the significant protein masses in the body, among them collagen, elastin, lens proteins, and the kidney glomerular basement membranes. These proteins deteriorate both with age (hence the application of the term "protein aging") and as one of the sequelae of diabetes melitis. Consequently, the ability to measure the amount of the formation of advanced glycosylation end products carries the promise of favorably treating significant adverse effects of aging and of diabetes at an earlier stage, and, of course, improving the quality and perhaps duration of animal life, including for instance human life.

Accordingly, it is a principal object of the present invention to provide a method for measuring the extent of cross-linking of amino-containing peptides, proteins, biomolecules or other compounds that occurs as an ultimate consequence of the reaction of said peptides, proteins, biomolecules or other compounds with glucose or other reducing sugars, by measuring therein the corresponding formation of the advanced glycosylation end products of the present invention. This method finds particular use, among other applications, in the diagnosis of glycation-related disease and the monitoring of anti-glycation therapy or prophylactic treatment.

It is a further object of the present invention to provide therapeutic methods which comprise administration of the advanced glycosylation products of the present invention to mammals in order to activate the mammalian macrophage system to increase their activity of recognizing and removing such advanced glycosylation endproducts.

It is a still further object of the present invention to provide diagnostic methods for screening for and measuring the extent of the adverse consequences of aging, manifest, for instance, in the stiffening and embrittlement of animal protein and the browning and spoilage of foodstuffs and other comestibles by measuring the amount of advanced glycosylation endproducts.

Other objects and advantages will become apparent to those skilled in the art from a consideration of the ensuing description which proceeds with reference to the following illustrative drawings.

DETAILED DESCRIPTION OF THE INVENTION

Figure 1:
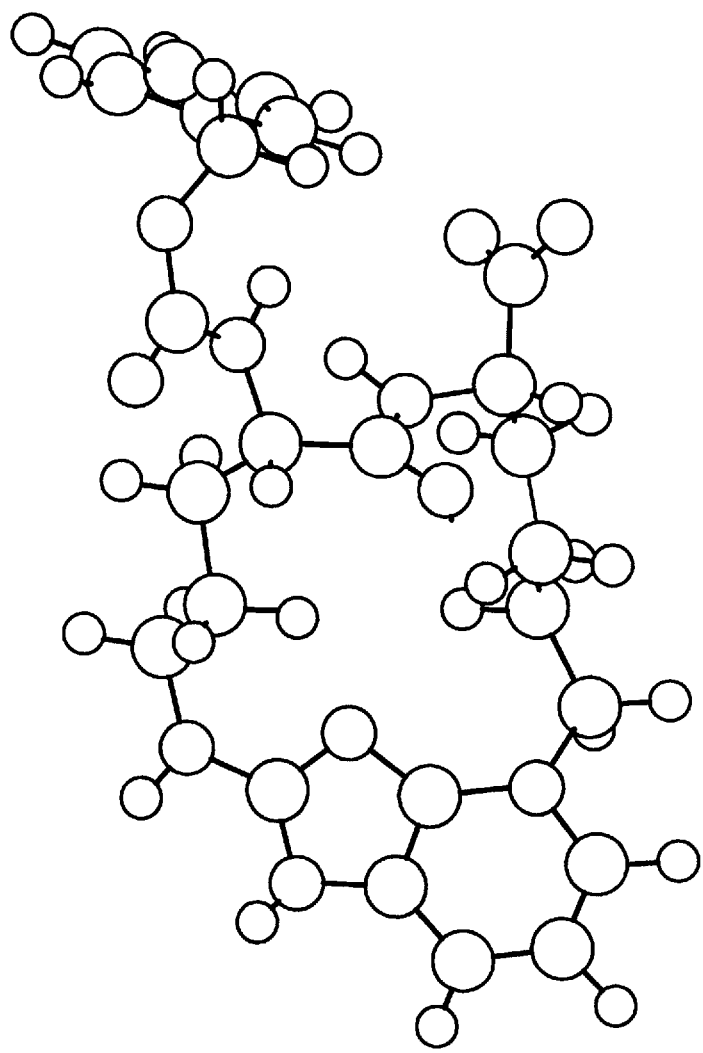
FIG. 1 is a energy minimized, molecular model of a cyclic pentosidine-RK dipeptide (Insight II and Discover Software, Biosym, Inc.). Force field potentials and charges were assigned automatically using parameters from the CVFF force field file. Energy minimization proceeded through the steepest descent method until the rms derivative fell below 0.01 kcal mol$^{-1}$A$^{-1}$.

In accordance with the present invention, Applicants have examined the contribution of intramolecular crosslinking of adjacent residues to the formation of pentosidine-type advanced glycosylation endproducts, using an arginine-lysine or lysine-arginine dipeptide, optionally as a portion of a peptide, protein or other biomolecule. In particular, the invention relates to compounds of the formulae I

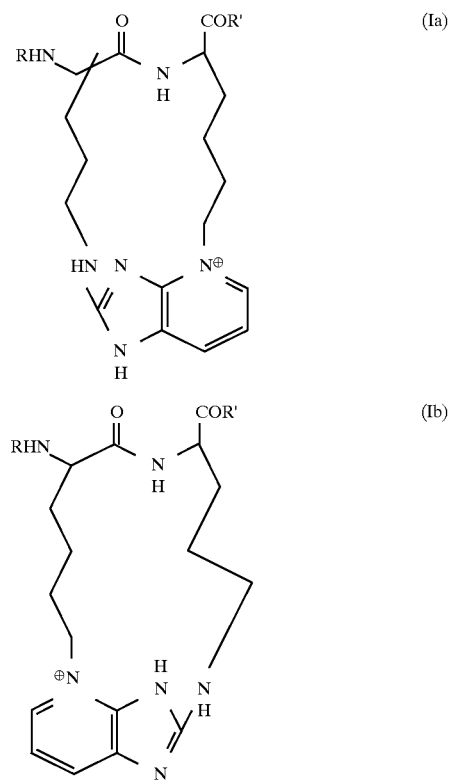

wherein R is hydrogen, an amino-protecting group, or the acyl terminus of an extension of the lysine-arginine- or arginine-lysine-containing peptide, protein or biomolecule; and R' is hydroxyl, or the amino terminus of an extension of the lysine-arginine- or arginine-lysine-containing peptide, protein or biomolecule, and to compositions which may contain them, as well as to their methods of use.

The compounds of formulae I are prepared by the incubation of an arginine-lysine or lysine-arginine dipeptide or dipeptide-containing peptide, protein or biomolecule, optionally containing an amino-protecting group, with a reducing sugar, such as ribose, glucose, fructose, or with ascorbate or dehydroascorbate at physiological pH for periods of about 10-100 hours, and optionally, at an elevated temperature of about 70° C for shorter periods of time. The thus formed compounds are then purified by HPLC to afford the cyclic pentosidine dipeptides of formulae I wherein R and R' are the residue of the peptide, protein or biomolecule.

The amine-blocking groups utilized in the present invention may be selected from any of the standard groups known in the art. Particularly preferred is the CBZ (carboxybenzyl) group due to its ease of removal and the retention of stereochemistry during manipulations using it.

In the instance where the present invention has therapeutic applications, the animal host intended for treatment may have administered to it a quantity of one or more of the advanced glycosylation endproducts of formulae I, either as a free cyclic pentosidine compound or formed within the sequence of a longer peptide or peptide-like molecule, in a suitable pharmaceutical form. Such administration can increase the macrophage recognition and elimination of other advanced glycosylation endproducts in the mammalian body. Administration may be accomplished by known techniques, such as oral, topical and parenteral techniques such as intradermal, subcutaneous, intravenous, or intraperitoneal injection, as well as by other conventional means such as inhaled aerosols or nebulized droplets. Administration of the agents may take place over an extended period of time at a dosage level of, for example, up to about 25 mg/kg.

The ability to measure the formation of advanced glycosylation end products carries with it significant implications in all applications where protein aging is a serious detriment. Thus, in the area of food technology, the facile determination of the amount of food spoilage allows for social benefit by ensuring that potentially harmful food products can be removed from use in a timely fashion. The expense of inspection, removal and replacement of the foods would be reduced due to the ease of making such determinations. Similarly, in other industrial applications where the perishability of proteins or other amino-containing biomolecules (e.g. lipids and DNA) or compounds (e.g. pharmaceutical compositions) is a problem, a measurement of the amount of AGE formation will provide a low-cost and facile method of determining shelf-life.

Accordingly, the compositions useful in the present invention comprise the compounds of formulae I, together with carriers suitable for their intended use.

The findings of the present invention can also be utilized to screen for additional agents which would have utility as agents for inhibiting advanced glycosylation or glycation. Thus, the measurement of the amount of the formation of the compound of formulae I when exposed to an amount of a potential inhibitor of the advanced glycosylation reaction, would enable one to assess the usefulness of an agent as a potential inhibitor of the advanced glycosylation or glycation process.

The compounds of formulae I may be used in standard fashion to prepare either polyclonal or monoclonal antibodies thereto for diagnostic purposes. Such antibodies are preparable by standard procedures, and thus enable the use of diagnostic assays for assessing and monitoring the effectiveness of therapeutic regimens where AGE inhibition has been initiated. Said immunological regents directed against generic and specific structures of the present invention are also useful to detect the degree of advanced glycosylation in a sample from a subject animal, including, for example, a human being, thereby to infer degree of advanced glycosylation which has occurred in the subject, by reference to a standard. Said polyclonal or monoclonal immunological reagents can optionally be included in a kit, with instructions, and, optionally, a standardized preparation of a cyclic pentosidine compound of the present invention, to facilitate such determinations all as contemplated hereunder.

In the instance where the composition of the present invention is utilized for in vivo or therapeutic purposes, it may be noted that the compounds or agents used therein are biocompatible. Pharmaceutical compositions may be prepared with a pharmaceutically effective quantity of the agents or compounds of the present invention and may include a pharmaceutically acceptable carrier, selected from known materials utilized for this purpose. Such compositions may be prepared in a variety of forms, depending on the method of administration. For example, a liquid form would be utilized in the instance where administration is by intravenous or intraperitoneal injection, which liquid might be aerosolized for delivery by inhalation; while, if appropriate, tablets, capsules, etc., may be prepared for oral administration. For application to the skin, a lotion or ointment may be formulated with the agent in a suitable vehicle, perhaps including a carrier to aid in penetration into the skin. Other suitable forms for administration to other body tissues are also contemplated.

In the instance where therapeutic applications are intended, the animals to be treated would have administered to them a regular quantity of the pharmaceutical composition of the present invention. Administration could take place, for example, daily, and an effective quantity of the agent or compound of the present invention could range up to 25 mg/kg of body weight of the animal. A topical preparation may, for example, include up to 10% of the agent or composition in an ointment or lotion for application to the skin. Naturally, some variation in these amounts is possible, and the suggested amounts are provided in fulfillment of applicants' duty to disclose the best mode for the practice of the present invention.

The in vivo therapeutic implications of the present invention relate to the reversal of several of the pathogenic activities associated with the aging process which have, as indicated earlier, been identified in the aging of key tissue and circulating proteins by advanced glycosylation and crosslinking through the mechanism of macrophage stimulation of the removal of the advanced glycosylation endproducts. Thus, body proteins, and particularly structural body proteins such as collagen, elastin, lens proteins, nerve proteins and kidney glomerular basement membranes would all benefit in their longevity and operation from the practice of the present invention. The present invention thus reduces the senescence caused by pathologies involving the entrapment of proteins by crosslinked target proteins, as exemplified, for instance, in retinopathy, cataracts, diabetic kidney disease, glomerulosclerosis, peripheral vascular disease, arteriosclerosis obliterans, peripheral neuropathy, stroke, hypertension, atherosclerosis, osteoarthritis, periarticular rigidity, loss of elasticity and wrinkling of skin, stiffening of joints, glomerulonephritis, etc. Likewise, all of these conditions are in evidence in patients afflicted with diabetes mellitus. Thus, the present therapeutic method is relevant to treatment of the noted conditions in patients either of advanced age or those suffering from one of the mentioned pathologies, particularly in association with hyperglycemia, which accelerates glycation-mediated senescence.

Protein crosslinking through advanced glycosylation product formation can decrease solubility of structural proteins such as collagen in vessel walls, and as well as trap serum proteins, such as lipoproteins to structural proteins such as collagen. Also, this may result in covalent trapping of extravasated plasma proteins in subendothelial matrix, and reduction in susceptibility of both plasma and matrix proteins to physiological degradation by enzymes. For these reasons, the progressive occlusion of diabetic vessels induced by chronic hyperglycemia has been hypothesized to result in part from excessive formation of glucose-derived adducts and crosslinks. Such diabetic macrovascular changes and microvascular occlusion can be effectively treated by enhancing the removal of advanced glycosylation endproducts utilizing a composition and the methods of the present invention.

The present invention will be better understood from a consideration of the following illustrative examples, reviewing the selection and testing of certain of the agents of the present invention on both an in vitro and in vivo basis.

This invention may be embodied in other forms or carried out in other ways without departing from the spirit or essential characteristics thereof. The present disclosure is therefor to be considered as in all respects illustrative and not restrictive, the scope of the invention being indicated by the appended Claims, and all changes which come within the meaning and range of equivalency are intended to be embraced therein.

Example 1

The arginine-lysine (RK) dipeptide was heated at 70° C. with two equivalents of D-ribose, D-glucose or D-fructose, in phosphate buffer for 48 hours. The incubations then were analyzed by HPLC with UV ($\lambda_{max}$ 320 nm) detection. In each case, a major peak with an identical elution time and the characteristic UV spectrum ($\lambda_{max}$ 320 nm) of pentosidine was evident. The MS spectra (m/z 361) and $^1$H-NMR spectra confirmed the structure of a pentosidine-RK condensation product formed by intramolecular crosslinking of the lysine $\epsilon$-amino group with the guanidino group of the adjacent arginine to form one of the cyclic pentosidine-like compounds of the present invention. Other peaks also were identified to be present in each incubation. These occurred in very low concentrations and were assigned the expected structure of a pentosidine moiety linking two molecules of RK (intermolecular crosslinks).

Example 2

In a second model study, the alpha-amino group of RK was protected in order to study the reactivity of the R and K side chains in a domain more closely resembling that of a native protein. The incubation of N-alpha-CBZ-RK with two equivalents of D-ribose in 0.2 M phosphate buffer (pH 7.4) for three weeks at 37° C. yielded pentosidine as a major fluorescent compound in 4.5% yield. Separation and purification of this compound was carried out by reverse phase HPLC. The $^1$H-NMR spectrum of the compound revealed, beside the protons of the starting material, three protons which resonate as an ABX system at $\delta$=7.85 (d, J=6.4 Hz), 7.67 (d, J=7.4 HZ) and 7.15 (bdd, J=7.2, 6.9 Hz), and which are consistent with the pentosidine structure. The electron spray (ES) mass spectrum showed a molecular ion at 495 (M) which is consistent with the molecular formula $C_{25}H_{51}N_6O_5$ (hrFAB 495.2482, calculated 495.2356).

The studies of Examples 1 and 2 supports the high reactivity of dibasic amino acid systems toward Maillard reactants and suggest a potentially active competition between intra- and intermolecular crosslink formation, both in vitro and in vivo. These data also may account for the low frequency of intermolecular crosslink and consequent pentosidine formation in certain protein substrates.

Example 3

Antigens, and conjugated immunogens corresponding to the cyclic pentosidine-like advanced glycosylation endproducts of the present invention, including the products described in Examples 1 and 2, can conveniently be prepared, either by isolation from incubation mixtures or by direct synthetic approaches. The AGEs thus prepared may then be used as an immunogens to raise a variety of antibodies which recognize specific epitopes or molecular features thereof. In a preferred embodiment, the cyclic pentosidine-RK or (KR) dipeptide itself is considered a hapten, which is correspondingly coupled to any of several preferred carrier proteins, including for instance keyhole limpet hemocyanin (KLH), thyroglobulin, and most preferred, bovine serum albumin (BSA), using any of a number of well-known divalent coupling reagents such as a carbodiimide like EDC, according to protocols widely circulated in the art. Alternatively, the desired cyclic pentosidine-RK dipeptide can be synthesized ab initio. Irrespective of the source, the cyclic pentosidine-like AGE (or ansa-macrocycle) of formulae I, alone or coupled to a carrier protein, may be employed in any well-recognized immunization protocol to generate antibodies and related immunological reagents that are useful in a number of applications owing to the specificity of the resulting antibodies for molecular features of the cyclic pentosidine-like AGE of formulae I.

Following a preferred protocol, any of several animal species may be immunized to produce polyclonal antisera directed against the cyclic pentosidine-like dipeptide-carrier protein conjugate, including for instance mice, rats, hamsters, goats, rabbits, and chickens. The first of three of the aforesaid animal species are particularly desired choices for the subsequent production of hybridomas secreting hapten-specific monoclonal antibodies. The production of said hybridomas from spleen cells of immunized animals may conveniently be accomplished by any of several protocols popularly practiced in the art, and which describe conditions suitable for immortalization of immunized spleen cells by fusion with an appropriate cell line, e.g. a myeloma cell line. Said protocols for producing hybridomas also provide methods for selecting and cloning immune splenocyte/myeloma cell hybridomas and for identifying hybridomas clones that stably secrete antibodies directed against the desired epitope(s). Animal species such as rabbit and goat are more commonly employed for the generation of polyclonal antisera, but regardless of whether polyclonal antisera or monoclonal antibodies are desired ultimately, the hapten-modified carrier protein typically is initially administered in conjunction with an adjuvant such as Complete Freund's Adjuvant. Immunizations may be administered by any of several routes, typically intraperitoneal, intramuscular or intradermal; certain routes are preferred in the art according to the species to be immunized and the type of antibody ultimately to be produced. Subsequently, booster immunizations are generally administered in conjunction with an adjuvant such as alum or Incomplete Freund's Adjuvant. Booster immunizations are administered at intervals after the initial immunization; generally one month is a suitable interval, with blood samples taken between one and two weeks after each booster immunization. Alternatively, a variety of so-called hyperimmunization schedules, which generally feature booster immunizations spaced closer together in time, are sometimes employed in an effort to produce anti-hapten antibodies preferentially over anti-carrier protein antibodies.

The antibody titers in post-boost blood samples can be compared for hapten-specific immune titer in any of several convenient formats including, for instance, Ouchterlony diffusion gels and direct ELISA protocols. In a typical direct ELISA, a defined antigen is immobilized onto the assay well surface, typically in a 96-well or microtiter plate format, followed by a series of incubations separated by rinses of the assay well surface to remove unbound binding partners. By way of non-limiting example, the wells of an assay plate may receive a dilute, buffered aqueous solution of the hapten/carrier conjugate, preferably wherein the carrier protein differs from that used to immunize the antibody-producing animal to be tested; e.g. serum from AGE/KLH conjugate-immunized animal might be tested against assay wells decorated with immobilized cyclic pentosidine-like AGE/BSA conjugate. Alternatively, the assay surface may be decorated by incubation with the hapten alone. Generally, the surface of the assay wells is then exposed to a solution of an irrelevant protein, such as casein, to block unoccupied sites on the plastic surfaces. After rinsing with a neutral buffered solution that typically contains salts and a detergent to minimize non-specific interactions, the well is then contacted with one of a serial dilution of the serum prepared from the blood sample of interest (the primary antiserum in crude or purified form). After rinsing again, the extent of test antibodies immobilized onto the assay wells by interaction with the desired hapten or hapten/carrier conjugate can be estimated by incubation with a commercially available enzyme-antibody conjugate, wherein the antibody portion of this secondary conjugate is directed against the species used to produce the primary antiserum; e.g. if the primary antiserum were raised in rabbits, a commercial preparation of anti-rabbit antibodies raised in goat and conjugated to one of several enzymes, such as horseradish peroxidase, can be used as the secondary antibody. Following procedures specified by the manufacturer, the amount of this secondary antibody can then be estimated quantitatively by the activity of the associated conjugate enzyme in an assay, typically a calorimetric assay. Many related ELISA or radioimmunometric protocols, such as competitive ELISAs or sandwich ELISAS, all of which are well-known in the art, may optionally be substituted, to identify the desired antisera of high titer; that is, the particular antiserum which gives a true positive result at high dilution (e.g. greater than 1/1000 and more preferably greater than 1/10,000).

Similar immunometric protocols can be used to estimate the titer of antibodies in culture supernatants from hybridomas prepared from spleen cells of immunized animals. In so characterizing antisera or hybridoma supernatants, it is desirable to employ a variety of control incubations, e.g. with different carrier proteins, related but structurally distinct haptens or antigens, and omitting various reagents in the immunometric procedure in order to minimize non-specific signals in the assay and to identify reliable determinations of antibody specificity and titer from false positive and false negative results. The types of control incubations to use in this regard are well known. Also, the same general immunometric protocols subsequently may be employed with the antisera identified by the above procedures to be of high titer and to be directed against specific structural determinants in the cyclic pentosidine-RK or KR dipeptide on biological samples, foodstuffs or other comestibles, or other amine-bearing substances and biomolecules of interest. Such latter applications of the desired antibodies, whether polyclonal or monoclonal, together with instructions and optionally with other useful reagents and diluents, including, without limitation, a set of molecular standards of the cyclic pentosidine-RK (or KR) dipeptide, may be provided in kit form for the convenience of the operator.

What is claimed is:

1. A compound of the formulae

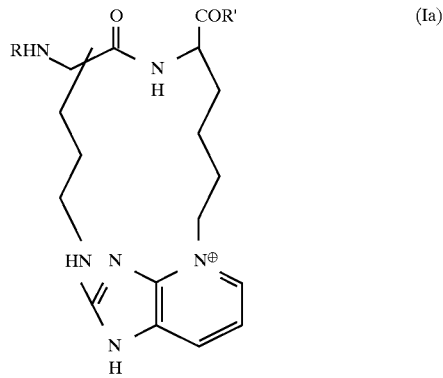

(Ia)

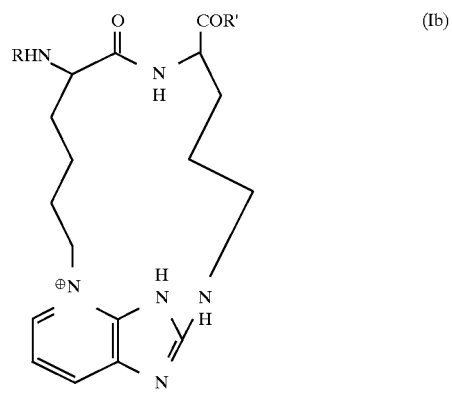

(Ib)

wherein said compound comprises the dipeptide lysyl-arginine or arginyl-lysine, or a peptide, protein, or biomolecule containing the subsequence lysyl-arginyl or arginyl-lysyl;

R is hydrogen, an amino-protecting group, an amino-terminal portion of the lysyl-arginyl - or arginyl-lysyl-containing peptide or protein. or an acyl group of said biomolecule; and R' is hydroxyl or a carboxy-terminal portion of the lysyl-arginyl- or arginyl-lysyl-containing peptide, protein or biomolecule.

2. The compound according to claim 1, which is cyclic pentosidine-RK dipeptide or cyclic pentosidine-KR dipeptide.

3. The compound according to claim 1, which is N-alpha-CBZ-cyclic pentosidine-RK dipeptide or N-alpha-CBZ-cyclic pentosidine-KR dipeptide.

4. A pharmaceutical composition adapted for increasing macrophage recognition and elimination of advanced glycosylation endproducts which comprises a therapeutic amount of the compound of claim 1, together with a pharmaceutically acceptable carrier therefor.

5. The composition of claim 4, which comprises cyclic pentosidine-RK dipeptide or cyclic pentosidine-KR dipeptide, together with a pharmaceutically acceptable carrier therefor.

6. The composition of claim 4, which comprises N-alpha-CBZ-cyclic pentosidine-RK dipeptide or N-alpha-CBZ-cyclic pentosidine-KR dipeptide, together with a pharmaceutically acceptable carrier therefor.

* * * * *